(12) United States Patent
Yamaguchi

(10) Patent No.: US 7,087,885 B1
(45) Date of Patent: Aug. 8, 2006

(54) PARTICLE SIZE DISTRIBUTION MEASURING APPARATUS AND METHOD

(75) Inventor: Tetsuji Yamaguchi, Kyoto (JP)

(73) Assignee: Horiba, Ltd., Kyoto (JP)

( * ) Notice: Subject to any disclaimer, the term of this patent is extended or adjusted under 35 U.S.C. 154(b) by 0 days.

(21) Appl. No.: 09/568,907

(22) Filed: May 11, 2000

(30) Foreign Application Priority Data

May 19, 1999 (JP) ............................................ 11-138035
Sep. 20, 1999 (JP) ............................................ 11-266182

(51) Int. Cl.
*G01V 8/00* (2006.01)

(52) U.S. Cl. ..................................... 250/222.2; 356/336
(58) Field of Classification Search .............. 250/222.2, 250/574; 356/336, 338, 342
See application file for complete search history.

(56) References Cited

U.S. PATENT DOCUMENTS

| | | | | |
|---|---|---|---|---|
| 5,416,580 A | * | 5/1995 | Trainer ........................ | 356/336 |
| 5,471,298 A | * | 11/1995 | Moriya ..................... | 250/222.2 |
| 5,861,951 A | * | 1/1999 | Uesugi et al. .............. | 356/338 |
| 6,091,492 A | * | 7/2000 | Strickland et al. .......... | 356/336 |
| 6,191,853 B1 | * | 2/2001 | Yamaguchi et al. ........ | 356/336 |

* cited by examiner

*Primary Examiner*—NIkita Wells
*Assistant Examiner*—James P. Hughes
(74) *Attorney, Agent, or Firm*—Brown Raysman Millstein Felder & Steiner LLP

(57) ABSTRACT

The present invention provides an apparatus for measuring particle distribution for determining particle size distribution with higher precision by compensating for a reduction in scattering light due to the color of a sample and due to the particle size characterized by Mie scattering theory, and a method for measuring particle size distribution using such an apparatus. The apparatus for measuring particle distribution irradiates a laser beam to be measured, converts the resulting scattering light into an electrical detection signal, and performs inverse operation processes on the detection signal to calculate the particle size distribution of the sample. The measuring apparatus is provided with a laser light source that variably changes the wavelength of the laser beam depending on samples. The measuring apparatus is further provided with a particle size distribution analysis section for calculating the particle size distribution of the sample by using scattering light from the sample that are obtained upon application of the laser beam having a wavelength that allows measurement of the strongest from scattering light the sample.

21 Claims, 4 Drawing Sheets

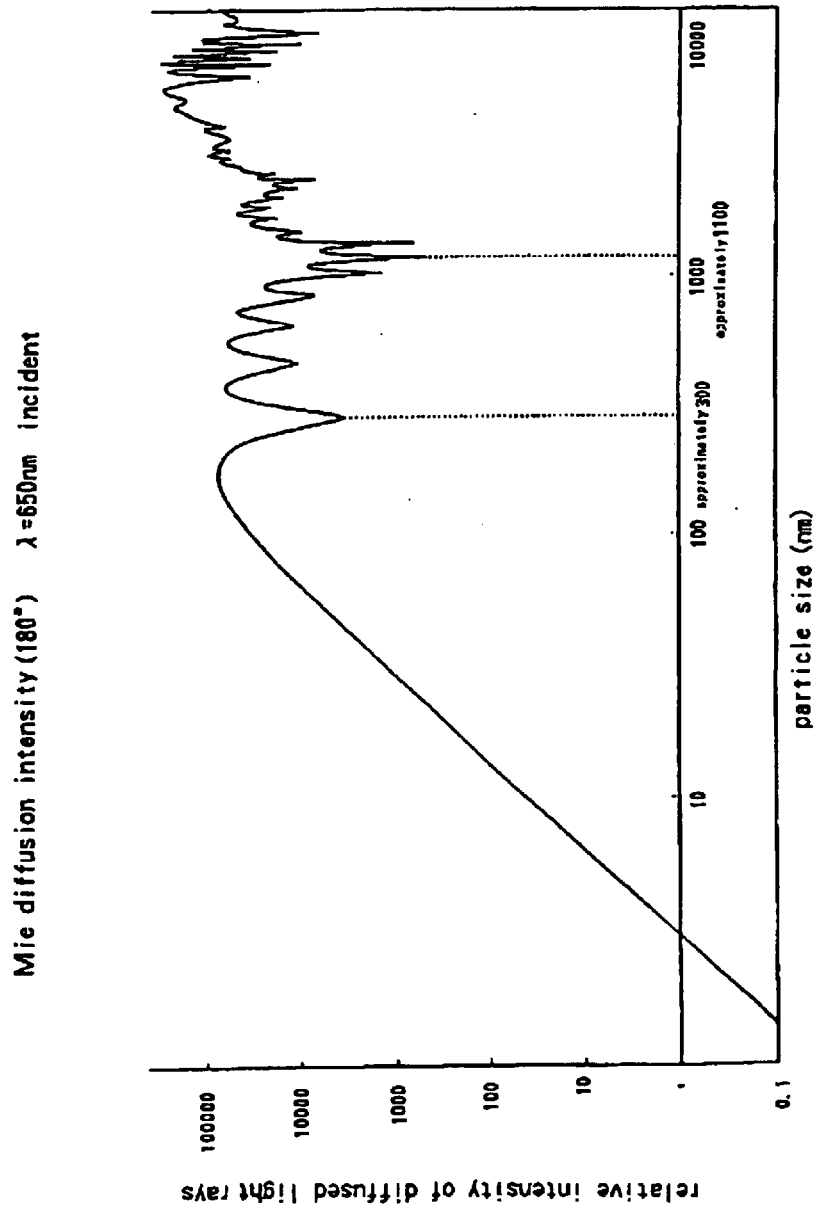

US 7,087,885 B1

PARTICLE SIZE DISTRIBUTION MEASURING APPARATUS AND METHOD

FIELD OF THE INVENTION

The present invention relates to an apparatus for measuring particle size distribution by dynamic light scattering.

DESCRIPTION OF THE PRIOR ART

In recent years, apparatuses for measuring particle size distribution, which measure the particle size distribution of particles dispersed in a solvent have been proposed. The measuring system of these apparatuses is described as follows: the apparatus for measuring particle size distribution directs a laser beam having a specific wavelength to the sample and detects a scattering light from the particles on a detector. Interference light of the scattering light, which is caused by a Doppler shift of the laser beam that is directed to the particles in Brownian motion, is detected. The detection signal of the scattering light is calculated by a Fourier transform so that its power spectrum is calculated. The relationship between the frequency and light intensity is obtained. Next, the particle size distribution is calculated by the power spectrum.

In the above-mentioned apparatus for measuring particle size distribution, the laser light source using, for example, a laser beam having a wavelength of 650 nm have been adopted. Although the laser source of this type is effective for particular samples to be measured, it tends to be ineffective for other samples to be measured due to its weak scattering light intensity. For example, in the case where the sample is colored since the laser beam is absorbed by the sample, scattering light intensity is too weak. Therefore, the measuring precision of the particle size distribution is highly dependent upon the color of the sample to be measured.

Moreover, the scattering light from each size particle depends on the wavelength of light. FIG. 6 is a graph that shows the scattering light intensity caused by each particle size, which is obtained through Mie's scattering theory. This case displays the scattering light intensity of a laser beam having a wavelength of 650 nm at the position of 180 degrees. As shown in FIG. 6, where a laser beam having a wavelength of 650 nm is used, approximately 300 nm and 1100 nm size particles display very weak scattering light intensity. For this reason, if inverse operation processes for calculating particle size distribution are carried out by using such weak scattering light intensity, the measurement precision will not be good.

SUMMARY OF THE INVENTION

The present invention has been devised so as to solve the above-mentioned problems, and its objective is to provide an apparatus for measuring particle size distribution which can find the particle size distribution with higher precision by avoiding a reduction of scattering light due to the color of a sample and due to the particle size characterized by Mie scattering theory, and a method for measuring particle size distribution using such an apparatus.

In order to achieve the above-mentioned, objective, the apparatus for measuring particle size distribution of the present invention, which directs a laser beam to a sample, converts the resulting scattering light intensity into an electrical detection signal and carries out inverse operation processes on the detection signal to calculate the particle size distribution. The measuring apparatus is characterized by being provided with a laser source for variably changing the wavelength of the laser beam to be applied depending on the samples. A particle size distribution analysis section analyzes the particle size distribution of the particles contained in the sample by using scattering light from the sample that are obtained upon application of the laser beam having a wavelength that allows measurement of the strongest scattering light from the sample to be measured. Here, the inverse operation processes refer to processes for obtaining the particle size distribution from an integral equation of Fredholm of a first type that is a relational expression among the power spectrum, response function and particle size distribution. This is distinct from deconvolution for finding the particle size distribution from convolution integration.

Therefore, since the wavelength of the laser beam to be irradiated is changed in accordance with the color of a sample and particle size, the scattering light intensity can be increased so that it becomes possible to measure the target particle size distribution more accurately. With respect to the wavelength of the laser beam, for example, those having light emissions of blue, green and red may be used for measuring samples having colors within the visible range. Moreover, with respect to black measuring samples that absorb all the visible light rays, those having light emissions of near infrared rays may be used.

Additionally, the applicant of the present application filed a patent application on Oct. 30, 1998, named "Particle Size Distribution Analyzing Method" (Japanese patent application no. 309978/1998 (Tokukaihei 10-309978), hereinafter, referred to as the prior application). In the prior application, a new analyzing method for measuring the particle size distribution by using a theoretical formula that are conformed to various measurement conditions was proposed. Here, even in the case where the wavelength of the laser beam to be irradiated is changed as in the case of the present invention, the analysis proposed in the prior application may be adopted so as to measure the particle size distribution with high precision.

In the case where the laser light source is provided with a plurality of laser light sources for outputting laser beams having respectively different wavelengths, it is possible to reduce production costs because each of the laser light sources have a simpler construction. Moreover, the irradiation of the laser beam and the receipt of scattering light may be carried out for each wavelength or may be carried out simultaneously. Moreover, an optical system for irradiating the laser light from each of the laser light sources to a sample with different angles may be installed. Thus, laser beams from the respective laser light sources are directed to a sample by using the respective optical systems so as to measure the particle size distribution.

In the case where laser beams from the laser light sources are selected and irradiated to the sample, a shielding plate for selectively directing the laser beams from the laser light sources to the sample may be installed. Alternatively, a reflection mirror for selectively irradiating the laser beams from the laser light sources to the sample may be installed. Moreover, the laser light sources may be shifted so as to selectively irradiate the laser beam to the sample.

The method for measuring a particle size distribution in accordance with present invention, which directs a laser beam to a sample, converts the resulting scattering light intensity into an electrical detection signal and performs inverse operation processes on the detection signal to calculate the particle size distribution, is provided with the steps of: variably changing the wavelength of the laser beam to be applied depending on samples, and analyzing the particle size distribution in the sample by using scattering light from the sample that are obtained upon irradiation of the laser beam having a wavelength that allows measurement of the strongest scattering light intensity from the sample.

Moreover, in order to change the wavelength of the laser beam, a plurality of laser light sources for irradiating laser beams having respectively different wavelengths may be used. Furthermore, in this case, the optical systems respectively attached to the laser light sources may be used for irradiating the laser beams from the respective laser light sources to the sample from different angles.

With respect to methods for selectively irradiating laser beams from the laser light sources to the sample, a shielding plate is used for selectively directing the laser beams from the laser light sources to the sample. Alternatively, a reflection mirror for selectively directing the laser beams from the laser light sources to the sample may be installed. Moreover, the laser light sources may be shifted so as to selectively irradiate the laser beam to the sample.

BRIEF DESCRIPTION OF THE DRAWINGS

FIG. 6 is a graph showing the relationship of scattering light intensity based upon Mie's scattering theory.

DETAILED DESCRIPTION OF THE PREFERRED EMBODIMENTS

Figure 1:
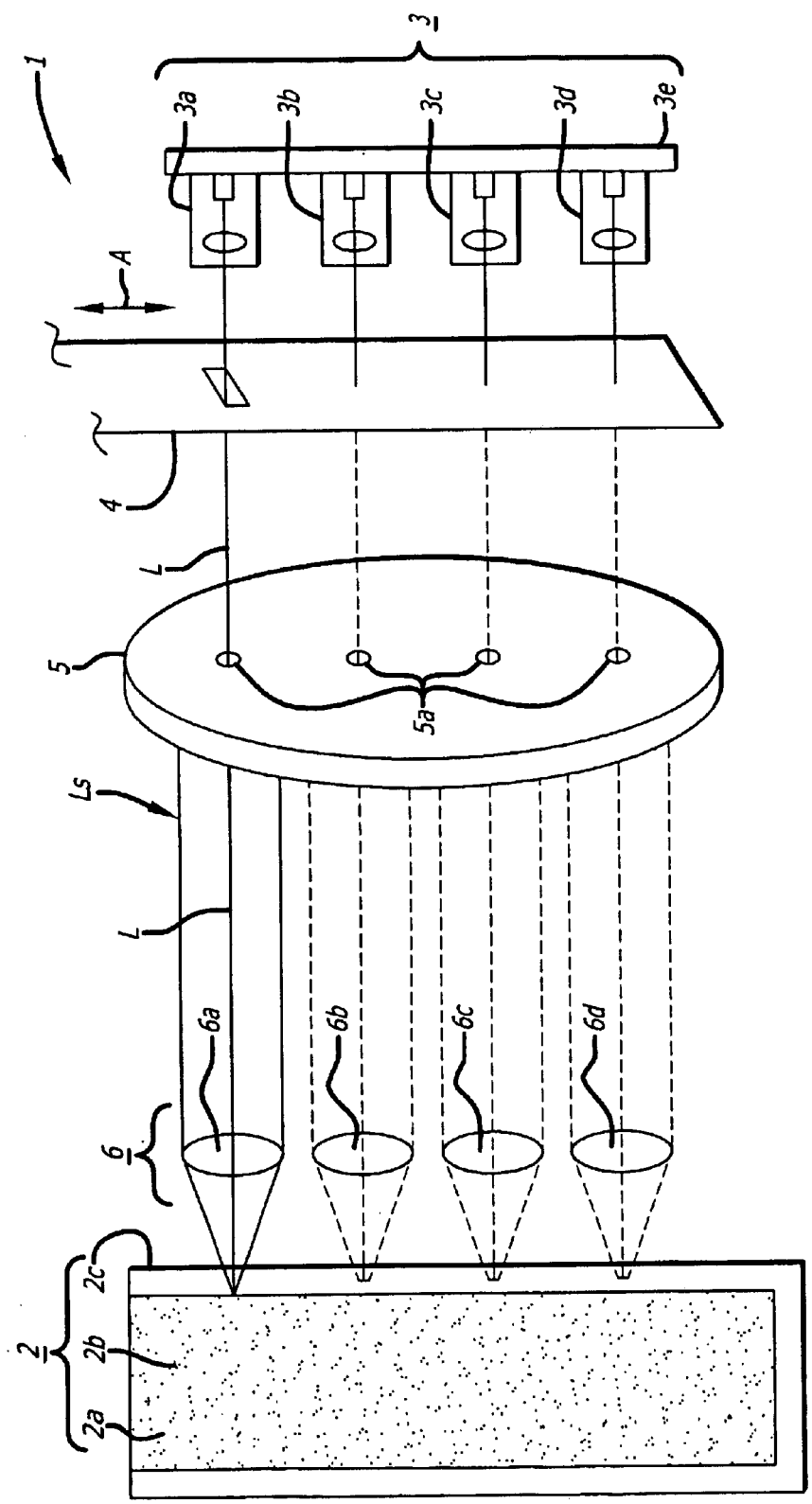
FIG. 1 is a schematic view of one embodiment of an apparatus for measuring particle size distribution in accordance with the present invention.
Figure 2:
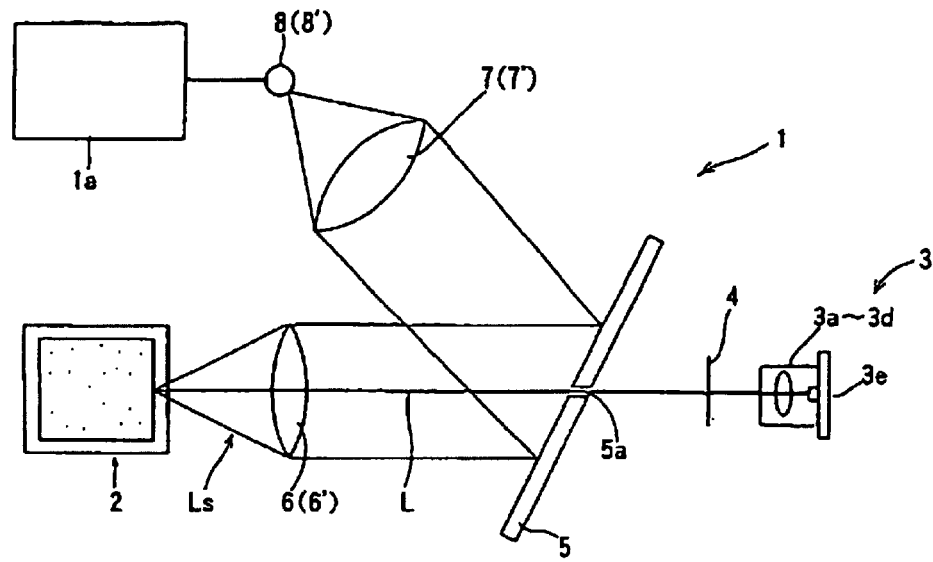
FIG. 2 is a schematic view of the apparatus for measuring particle size distribution viewed from another angle.

FIGS. 1 and 2 are schematic views that show essential portions of an apparatus for measuring particle size distribution 1 in accordance with a first embodiment of the present invention. In FIGS. 1 and 2, reference number 2 is a sample to be measured (hereinafter, referred to as sample), which is, for example, constituted by particles 2a to be measured, a solvent 2b and a cell 2c.

Reference number 3 is a laser light sources which can change the wavelength of the laser beam L to be irradiated to the sample 2. In the present embodiment, the light sources 3 is provided with laser diodes 3a to 3d for respectively irradiating laser beams L of red, green, blue and near infrared, and a common PCB (printed circuit board) 3e to which these laser diodes 3a to 3d are attached. Reference number 4 is a shielding plate hereinafter, referred to as shutter) for selectively directing the laser beams L from the laser diodes 3a to 3d; reference number 5 is a reflection mirror having a hole 5a through which the laser beam L is allowed to pass. FIG. 1 shows a lens system 6 comprising lens 6a, 6b, 6c and 6d which directs the laser beam L that has passed through the hole 5a to the sample 2 and collimate the scattering light Ls from the sample 2.

Moreover, as illustrated in FIG. 2, reference number 7 is a lens for collecting the scattering light Ls reflected by the reflection mirror 5 into four detectors 8 corresponding to the respective diodes 3a to 3d. In accordance with the apparatus for measuring particle size distribution 1 having the above-mentioned optical system, the shutter 4 is allowed to slide in directions indicated by two-sided arrow A (see FIG. 1) so that laser beams L having respectively different wavelengths are made incident on the sample 2. Thus, the intensity of the scattering light Ls are measured by the detectors 8. Reference number 1a is a particle size distribution calculating section for analyzing the particle size distribution by carrying out inverse operation processes on detection signals from these detectors 8.

At this time, the intensity of the scattering light Ls, which is affected by the color of the sample particle 2a and a reduction in the scattering light Ls caused by Mie scattering theory, is changed by the wavelength of the laser beam L. Therefore, in the apparatus for measuring particle size distribution 1 of the present embodiment, the intensity of the scattering light Ls to be measured by the detectors 8 is compared by successively switching the shutter 4.

Then, in the apparatus for measuring particle size distribution 1, the laser diode which applies the laser beat L having a wavelength for obtaining the strongest scattering light Ls is selected. The shutter 4 is controlled to allow only the laser beam from the resulting laser diode to be transmitted. Here, the wavelength of the laser beam L, which is irradiated by the selected laser diode, is used to calculate a response function for inverse operation processes, as data required for the calculations on the particle size distribution, together with various measurement conditions.

Additionally, with respect to the method for inverse operations, the method disclosed in the prior invention by the applicant of the present invention may be adopted. Thus, even if the wavelength of the laser beam L is changed, operations can be calculated with high precision by carrying out inverse operation processes to recalculate the wavelength of the laser beam L.

Moreover, in accordance with the apparatus for measuring particle size distribution 1 of the present embodiment, the wavelength corresponding to measurement of the strongest scattering light Ls is selected and irradiated to the sample 2; Therefore, it is possible to avoid effects caused by the absorption of the laser beam L dependent on the color of the sample 2a and by reduction of scattering light intensity by Mie's scattering theory. In other words, it is possible to variably measure the particle size distribution with high precision.

Additionally, in the above-mentioned embodiment, the laser light sources 3 that can change the wavelength is constituted by a PCB 3e on which the semiconductor laser diodes 3a to 3d of red, green, blue and near infrared are aligned in a single row. However, the construction of the laser light sources 3 that can change the wavelength of the present invention is not intended to be limited by this construction. For example, the number in which the wavelength can be changed may be set not to four wavelengths, but to five wavelengths or more wavelengths. Moreover, if it is enough to measure with high precision, this number may be set to not more than 3 wavelengths.

Moreover, in the present embodiment, the laser diodes 3a to 3d are aligned on one PCB 3e so that the light emitting control circuit for the laser diodes 3a to 3d are commonly used, thereby making it possible to simplify the circuit. However, the control circuit may of course be formed for each of the laser diodes 3a to 3d. In addition, a helium neon laser may be included in the laser light sources 3, or one pigment laser, which can emit laser beams having a plurality of wavelengths, may be used.

Moreover, in the above-mentioned embodiment, the laser beams L, which are emitted from the respective laser diodes 3a to 3d, are measured by the independent detectors 8. Therefore, by removing the shutter 4, scattering light Ls may be measured simultaneously. In this case, the measurement time of the particle size distribution may be shortened, or the analysis of the particle size distribution may be conducted by systematically judging the scattering light Ls of the respective wavelengths.

Here, it is noted that the present invention is not intended to be limited with respect to the optical constituent parts such as the shutter 4, the reflection mirror 5, the lens 6, 7 and detectors 8.

Figure 3:
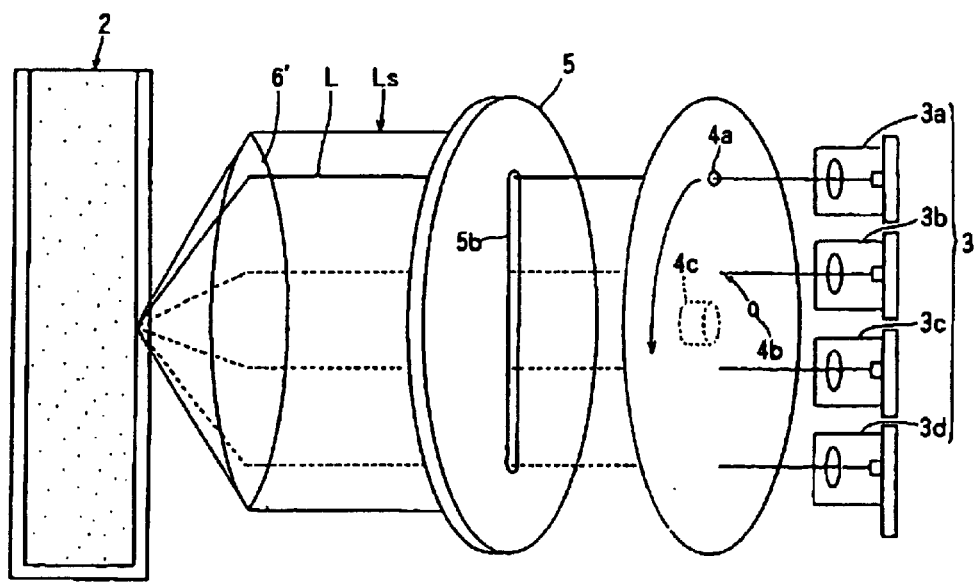
FIG. 3 is a schematic view of a modified example of the apparatus for measuring particle size distribution.

Moreover, as illustrated in FIG. 3, the shutter 4 may include holes 4a and 4b, and the laser beam L, which is transmitted through the rotation thereof by a motor 4c, may be selected. Furthermore, the reflection mirror 5 may be provided with slits 5b that are formed in accordance with the respective laser diodes 3a to 3d. Alternatively, a large diameter lens 6' for irradiating the laser beams L from the laser diodes 3a to 3d to the sample 2 may be utilized so that a single large lens replaces a plurality of smaller lenses.

As illustrated in FIG. 2, a lens with a large diameter may also be used as the lens 7' for receiving the diffused light rays Ls. Thus, the lens 7' and the detector 8' may be integrated into a single part. In other words, it is possible to simplify the construction of the apparatus for measuring particle size distribution 1.

Figure 4:
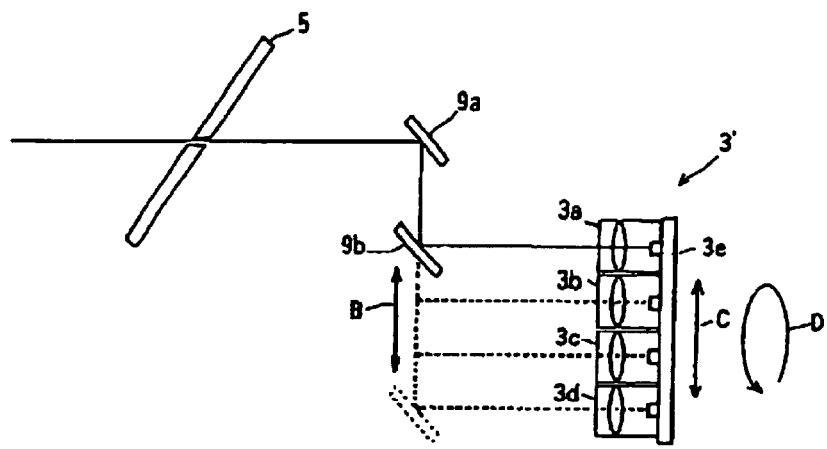
FIG. 4 is a schematic view of a modified example of a laser light source of the apparatus for measuring particle size distribution.

FIG. 4 is a schematic view that shows another example of one portion of the laser light sources 3' that can change the wavelength of the laser beam L to be applied. In FIG. 4, reference numbers 9a and 9b represent reflection mirrors. The reflection mirrors 9a and 9b allows the laser beams L from the laser diodes 3a to 3d to be selectively directed to the sample 2. In other words, for example, the reflection mirror 9a is fixed, and the reflection mirror 9b is allowed to slide as indicated by two-sided arrow B. Thus, it becomes possible to select one of the laser diodes 3a to 3d and direct the laser beam from the laser diode 3a to 3d to the sample 2.

Moreover, the reflection mirror 9b may be fixed, and the laser diodes 3a to 3d may be allowed to slide as indicated by two-sided arrow C together with the PCB 3e. Thus, a laser beam L from any one of the laser diodes 3a to 3d may be directed to the sample 2. Here, the method for shifting the laser diodes 3a to 3d is not particularly limited. As indicated by arrow D, the laser diodes 3a to 3d may be allowed to pivot.

Figure 5:
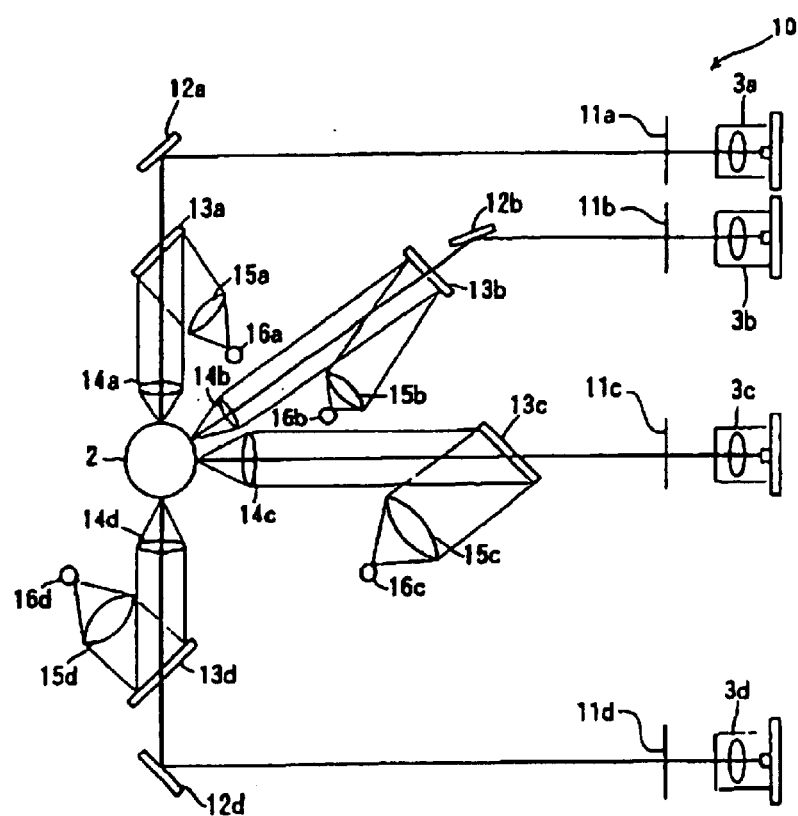
FIG. 5 is a schematic view of a modified example of an optical system of the apparatus for measuring particle size distribution.

FIG. 5 shows another example of an optical system 10. In the present embodiment, the optical system 10, which directs the laser beams L from the laser light sources 3a to 3d to the sample 2 from different angles, is provided. In other words, a plurality of shutters 11a to 11d are provided which correspond to the respective laser light sources 3a to 3d, reflection mirrors 12a, 12b, and 12d, reflection mirrors 13a to 13d, lenses 14a to 14d, 15a to 15d and detectors 16a to 16d.

Here, in the present embodiment, by changing the irradiating position of the laser beams L without the need for the shutters 11a to 11d, a plurality of laser beams L having different wavelengths can be irradiated to the sample.

In the above-mentioned arrangements shown in FIGS. 1 to 5, which include the laser light sources 3, 3', shutters 4, 11a to 11d, reflection mirrors 5, 13a to 13d, lenses 6, 6', 7, 7', 14a to 14d, 15a to 15d, and reflection mirrors 9a, 9b, 12a, 12b, 12d, are only specific examples showing the construction of an apparatus for measuring particle size distribution 1 utilizing dynamic light scattering from the laser beam L, wherein several kinds of laser light sources 3a to 3e having different wavelengths are assembled, and wherein the laser beam L that is not absorbed by a colored sample 2 is made incident thereon so that scattering light Ls having an intensity that enables an analysis with high precision are detected. Therefore, the present invention is not intended to be limited by the above-mentioned combinations and a desirable combination may be made with the same effects.

As described above, in accordance with the present invention, the wavelength of the laser beam is altered depending on the color of a sample and the size of particles to be measured so that, even when a sample to be measured tends to absorb a laser beam having a specific wavelength, the intensity of scattering light can be increased. In other words, it becomes possible to improve the measuring precision of the apparatus for measuring particle size distribution.

In the case where the laser light source is provided as a plurality of laser light sources that irradiate laser beams having respectively different wavelengths, the construction of each of the laser light sources is simplified. Therefore, it is possible to reduce production costs.

What is claimed is:

1. An apparatus for measuring particle size distribution by irradiating a laser beam to a sample, converting scattering light into an electrical detection signal, and performing inverse operation processes on the detection signal to calculate the particle size distribution of the sample, comprising:
    a laser light source capable of emitting multiple wavelengths of laser light for irradiating a sample; and
    a particle size distribution analysis section for calculating the particle size distribution of the sample using dynamic light scattering, the particle size distribution analysis section configured to measure a strongest wavelength of scattering light from the sample.

2. The apparatus for measuring particle size distribution of claim 1, wherein the laser light source includes a plurality of laser light sources for outputting laser beams having respectively different wavelengths.

3. The apparatus for measuring particle size distribution of claim 2, further comprising an optical system adapted to irradiate the laser light from each of the laser light sources at different angles.

4. The apparatus for measuring particle size distribution of claim 2, further comprising a shielding plate adapted to selectively irradiate the laser beams from the laser light sources to the sample.

5. The apparatus for measuring particle size distribution of claim 3, further comprising a shielding plate adapted to selectively irradiate the laser beams from the laser sources sections to the sample.

6. The apparatus for measuring particle size distribution of claim 2, further comprising a reflection mirror adapted to selectively irradiate the laser beams from the laser light sources to the sample.

7. The apparatus for measuring particle size distribution of claim 3, further comprising a reflection mirror adapted to selectively irradiate the laser beams from the laser light sources to the sample.

8. The apparatus for measuring particle size distribution of claim 2, wherein the laser light source includes a shiftable element to selectively irradiating the laser beam to the sample.

9. The apparatus for measuring particle size distribution of claim 3, wherein the laser light source includes a shiftable element to selectively irradiate the laser beam to the sample.

10. A method of measuring particle size distribution by irradiating a laser beam to a sample, converting resulting scattering light into an electrical detection signal, and performing inverse operation processes on the detection signal to calculate the particle size distribution of the sample, comprising:

using multiple wavelengths of laser light to irradiate a sample; and analyzing the particle size distribution of the sample by using dynamic scattering light from the sample, the dynamic scattering light having a wavelength that allows measurement of the strongest scattering light from the sample.

11. The method of claim 10, further comprising:

providing a plurality of laser light sources; and changing the wavelength of the laser beam by having the plurality of laser light sources irradiate laser beams having respectively different wavelengths.

12. The method of claim 11, further comprising:

attaching an optical system to a laser light source; and using the optical system to irradiate the laser beams from the laser light source to the sample from different angles.

13. The method of claim 10, further comprising:

providing a shielding plate; and using the shielding plate to selectively irradiate laser beams from the laser light sources to the sample.

14. The method of claim 11, further comprising:

providing a shielding plate; and using the shielding plate to selectively irradiate the laser beams from the laser light sources to the sample.

15. The method of claim 10, further comprising;

providing a reflection mirror to selectively irradiate the laser beams from laser light sources to the sample.

16. The method of claim 11, further comprising;

providing a reflection mirror to selectively irradiate the laser beams from laser the light sources to the sample.

17. The method of claim 10, further comprising:

shifting a laser light source to selectively irradiate the laser beam to the sample.

18. The method of claim 11, further comprising:

shifting the laser light source to selectively irradiate the laser beam to the sample.

19. An apparatus for measuring particle size distribution, comprising:

a multiple wavelength laser light source;

a shielding plate capable of selectively directing a wavelength of the laser light to a sample;

at least one detector configured to measure scattering light for each wavelength scattered by the sample; and a particle size distribution analysis section for calculating a particle size distribution of the sample in communication with said at least one detector, said particle size distribution analysis section capable of calculating said particle size distribution based on the wavelength of the scattered light measured by said at least one detector.

20. A method of measuring particle size distribution, comprising:

irradiating a sample with a multiple wavelengths of laser light;

measuring scattering light for each wavelength scattered by said sample with at least one detector to wavelength specific electrical detection signal;

selecting a strongest wavelength specific electrical detection signal measured by said at least one detector;

performing an inverse operation process on the selected wavelength specific electrical detection signal; and analyzing a particle size distribution of said sample based on said selected wavelength specific electrical detection signal.

21. An apparatus for measuring particle size distribution by irradiating a laser beam to a sample, converting scattering light into an electrical detection signal, and performing inverse operation processes on the detection signal to calculate the particle size distribution of the sample, comprising:

a laser light source capable of emitting multiple wavelengths of laser light for irradiating a sample;

a detector for measuring dynamic light scattering from the sample irradiated with the laser light; and a particle size distribution analysis section for calculating the particle size distribution of the sample, the particle size distribution analysis section configured to calculate the particle size distribution by calculating a power spectrum of the measured dynamic light and using an integral of a Fredholm equation to determine a relationship between the power spectrum and the particle size distribution.

\* \* \* \* \*